(12) United States Patent
Driehuys

(10) Patent No.: US 6,599,497 B2
(45) Date of Patent: Jul. 29, 2003

(54) HYPERPOLARIZED HELIUM-3 MICROBUBBLE GAS ENTRAPMENT METHODS AND ASSOCIATED PRODUCTS

(75) Inventor: Bastiaan Driehuys, Durham, NC (US)

(73) Assignee: Medi-Physics, Inc., Princeton, NJ (US)

( * ) Notice: Subject to any disclaimer, the term of this patent is extended or adjusted under 35 U.S.C. 154(b) by 10 days.

(21) Appl. No.: 09/894,768

(22) Filed: Jun. 28, 2001

(65) Prior Publication Data

US 2001/0051132 A1 Dec. 13, 2001

Related U.S. Application Data

(62) Division of application No. 09/428,814, filed on Oct. 28, 1999, now Pat. No. 6,284,222.
(60) Provisional application No. 60/106,843, filed on Nov. 3, 1998.

(51) Int. Cl.$^7$ ............................................. A61B 5/055
(52) U.S. Cl. ..................... 424/9.3; 424/9.32; 436/173
(58) Field of Search ............................. 424/9.3, 9.32, 424/9.52; 534/7; 436/173

(56) References Cited

U.S. PATENT DOCUMENTS

| | | | |
|---|---|---|---|
| 3,657,363 A | 4/1972 | Dorko | 260/642 |
| 3,966,781 A | 6/1976 | Atkinson et al. | 260/410.9 R |
| 3,989,705 A | 11/1976 | Werstiuk et al. | 260/290 P |
| 4,417,909 A | 11/1983 | Weltmer, Jr. | 62/12 |
| 4,450,407 A | 5/1984 | Kwon et al. | 324/304 |
| 4,466,442 A | 8/1984 | Hilmann et al. | 128/653 |
| 4,586,511 A | 5/1986 | Clark, Jr. | 128/653 |
| 4,599,462 A | 7/1986 | Michl | 568/702 |
| 4,755,201 A | 7/1988 | Eschwey | 62/12 |
| 4,775,522 A | 10/1988 | Clark, Jr. | 424/9 |
| 4,793,357 A | 12/1988 | Lindstrom | 128/654 |
| 4,862,359 A | 8/1989 | Trivedi et al. | 364/413.05 |
| 4,914,160 A | 4/1990 | Azizian | 525/329.3 |
| 4,977,749 A | 12/1990 | Sercel | 62/51.1 |
| 4,996,041 A | 2/1991 | Arai et al. | 424/9 |
| 5,039,500 A | 8/1991 | Shino et al. | 423/262 |
| 5,190,744 A | 3/1993 | Rocklage et al. | 424/9 |
| 5,322,511 A | 6/1994 | Armbruster et al. | 604/155 |
| 5,352,979 A | 10/1994 | Conturo | 324/307 |
| 5,494,655 A | 2/1996 | Rocklage et al. | 424/9.36 |
| 5,509,412 A | 4/1996 | Bahn | 128/653.2 |
| 5,545,396 A | 8/1996 | Albert et al. | 424/93 |
| 5,612,103 A | 3/1997 | Driehuys et al. | 428/34.7 |
| 5,617,860 A | 4/1997 | Chupp et al. | 128/653.4 |
| 5,642,625 A | 7/1997 | Cates, Jr. et al. | 62/55.5 |
| 5,773,024 A | 6/1998 | Unger et al. | 424/450 |
| 5,785,953 A | 7/1998 | Albert et al. | 424/93 |
| 5,809,801 A | 9/1998 | Cates, Jr. et al. | 62/637 |
| 5,833,947 A | 11/1998 | Rocklage et al. | 424/9.36 |
| 6,028,066 A * | 2/2000 | Unger | 514/180 |
| 6,033,645 A | 3/2000 | Unger et al. | 424/9.5 |
| 6,042,809 A | 3/2000 | Tournier et al. | 424/9.3 |
| 6,051,208 A | 4/2000 | Johnson et al. | 424/9.3 |
| 6,085,743 A | 7/2000 | Rosen et al. | 128/200.24 |
| 6,217,850 B1 * | 4/2001 | Dugstad et al. | 424/9.52 |
| 6,284,222 B1 | 9/2001 | Driehuys | 424/9.3 |
| 6,286,319 B1 | 9/2001 | Hasson et al. | 62/49.1 |

FOREIGN PATENT DOCUMENTS

| | | |
|---|---|---|
| DE | 27 58 855 A1 | 7/1979 |
| DE | 196 19471 C1 | 10/1997 |
| EP | 0 077 752 A2 | 4/1983 |
| EP | 0 357 163 A1 | 3/1990 |
| EP | 0495287 A2 | 7/1992 |
| EP | 0620447 A2 | 10/1994 |
| EP | 0933062 A2 | 8/1999 |
| WO | WO96/28090 | 9/1996 |
| WO | WO97/00638 | 1/1997 |
| WO | WO 97/29836 | 4/1997 |
| WO | WO 97/37239 | 10/1997 |
| WO | WO98/02209 A2 | 1/1998 |
| WO | WO 98/58272 | 12/1998 |
| WO | WO 99/07415 | 2/1999 |
| WO | WO99/08941 | 2/1999 |
| WO | WO 99/14582 | 3/1999 |
| WO | WO 99/17304 | 4/1999 |
| WO | WO99/25243 | 5/1999 |
| WO | WO 99/25243 | 5/1999 |
| WO | WO99/35508 | 7/1999 |
| WO | WO 99/52428 | 10/1999 |
| WO | WO99/52428 | 10/1999 |
| WO | WO 99/53332 | 10/1999 |

OTHER PUBLICATIONS

Albert et al., "$^{129}$Xe Relaxation Catalysis by Oxygen", Abstracts of the 11th Annual Meetings of the Society for Magnetic Resonance Medicine, Abstract No. 4710 (1992).
Albert et al., "Biological magnetic resonance imaging using laser–polarized $^{129}$Xe," Letters to Nature, vol. 370, pp. 199–201 (Jul. 21, 1994).
Albert et al., "Relaxation of $^{129}$Xe in Model Biological Systems: On Probing the Mechanism of General Anesthesia", Abstracts of the 11th Annual Meetings of the Society for Magnetic Resonance Medicine, Abstract No. 2104 (1992).

(List continued on next page.)

Primary Examiner—Michael G. Hartley
(74) Attorney, Agent, or Firm—Myers Bigel Sibley & Sajovec PA

(57) ABSTRACT

Methods for increasing the $T_1$ of injectable microbubble formulations of hyperpolarized $^3$He include the step of introducing the hyperpolarized $^3$He to a quantity of microbubbles held in a chamber and increasing the pressure therein to facilitate the movement or loading of the $^3$He into the microbubbles. Subsequently, a limited quantity of carrier liquid or a carrier liquid solution alone, or pre-mixed with $^3$He, can be introduced to the microbubble/$^3$He in the chamber to inhibit the tendency of the $^3$He to leach out of the bubble. Related pharmaceutical products and associated containers as well as an evacuation based method for rapid mixing and delivery of the bubbles and the $^3$He is also disclosed. An additional method for dissolving $^{129}$Xe gas by using bubbles as an accelerant is also described.

41 Claims, 5 Drawing Sheets

OTHER PUBLICATIONS

Albert et al., "Development of Hyperpolarized Nobel Gas MRI," Nucl. Inst. and Meth. in Phys. Res. A 402, pp. 441–453 (1998).

Albert et al., "Measurement of $^{129}$Xe T1 in Blood to Explore the Feasibility of Hyperpolarized $^{129}$Xe MRI," Jour. Comp. Ass. Tomography, vol. 19, No. 6 (Nov.–Dec. 1995).

Altschuler et al., "Radiobiologic Models for Radiosurgery," Neurosurg. Clin. N. Am., vol. 3, No. 1, pp. 61–77 (Jan. 1992).

Augustine et al., "Low Field Magnetic Resonance Images of Polarized Nobel Gases Obtained with a dc Quantum Interference Device," App. Phys. Ltrs., vol. 72, No. 15, pp. 1908–1910 (Apr. 1998).

Bárány, M. et al., "High Resolution Proton Magnetic Resonance Spectroscopy of Human Brain and Liver," Magn. Reson. Imaging, 5:393 (1987).

Belliveau et al., "Functional Cerebral Imaging by Susceptibility–Contrast NMR," 14 Magnetic Resonance in Medicine 14, pp. 538–546 (1990).

Bifone, et al., "NMR of laser–polarized xenon in human blood," Proc. Natl. Acad. Sci. USA, vol. 93, pp. 12932–12936 (Nov. 1996).

Bishop et al., "High–Order Multipolar Hyperpolarizabilities with Imaginary Frequency for H and He," Int'l Jour. of Quan. Chem., vol. 59, pp. 103–108 (1996).

Bock, "Simultaneous $T_2$* and Diffusion Measurements with $^3$He," Mag. Reson. in Med., vol. 38, No. 6, pp. 890–895 (1997).

Bishop et al., "The Interaction Polarizatility and Interaction Second–Hyperpolarizability for He . . . He," Molecular Phys., vol. 88, No. 4, pp. 887–898 (1996).

Bouchiat et al., "Relaxation of Optically Pumped Rb Atoms on Paraffin–Coated Walls," Phys. Rev., vol. 147, No. 1 (Jul. 8, 1966).

Brunner et al., "Communications: Gas Flow MRI Using Circulating Laser–Polarized $^{129}$Xe," J. Mag. Res. vol. 138, pp. 155–159 (1999).

Burt et al., "Fluorinated Anesthetics as Probes of Lipophilic Environments in Tumors," J. Magn. Reson., 53:163 (1983).

Cates et al., "Laser Production of Large Nuclear–Spin Polarization in Frozen Xenon", Phys. Rev. Lett., vol. 65, No. 20, pp. 2591–2594 (1990).

Cates et al., "Rb–$^{129}$Xe spin–exchange rates due to binary and three–body collisions at High Xe pressures", Physical Review A, vol. 45, p. 4631 (1992).

Cates, *New Results from Spin–Exchange Optical Pumping*, Am. Inst. Phys. pp. 3–15 (1998).

Chawla, et al., *In Vivo Magnetic Resonance Vascular Imaging Using Laser–Polarized 3He Microbubbles*, Proc. Natl. Acad. Sci, vol. 95, pp. 10832–18035 (Sep. 1998).

Chen et al., "MR Microscopy of Lung Airways with Hyperpolarides $^3$He," Mag. Reson. in Med., vol. 39, No. 1, pp. 79–84 (Jan. 1998).

Detre et al., "Measurement of Regional Cerebral Blood Flow in Cat Brain Using Intracartoid $^2$H$_2$O and $^2$H NMR Imaging," 14 Mag. Reson. in Med., pp. 389–395 (1990).

Diehl et al., "Nuclear Magnetic Relaxation of the $^{129}$Xe and $^{131}$Xe Isotopes of Xenon Gas Dissolved in Isotropic and Anisotropic Liquids," J. Magn. Reson., vol. 88, pp. 660–665 (1990).

Dodell, The Look of Lungs, NCRR Reporter, 3 pages (Nov./Dec. 1995), http://ch.nus.sg/MEDNEWS/feb96/hicn9095_7.htn.

Driehuys et al., "Surface Relaxation Mechanisms of Laser–Polarized 129Xe," 74 Phys. Rev. Lett., No. 24, pp. 4943–4946 (Jun. 12, 1995).

Evers et al., "Correlation between the anaesthetic effect of halothane and saturable binding in brain," Nature, vol. 328, pp. 157–160 (Jul. 9, 1987).

Freed, "Dynamic Effects of Pair Correlation Functions on Spin Relaxation by Translational Diffusion in Liquids. II. Finite Jumps and Independent $T_1$ Processes," 68 J. Chem. Phys., vol. 9, pp. 4034–4037 (1978).

Fullerton et al., Chapter 3 "Relaxation of Biological Tissues," Biomedical Magnetic Resonance Imaging: Principles, Methodology, and Applications, pp. 115–155, (1988).

Gao et al., "Magnetization and Diffusion Effects in NMR Imaging of Hyperpolarized Substances," Mag. Reson. in Med., vol. 37, No. 1 pp. 153–158 (Jan. 1997).

George, "The Sharper Image: MRIs and Xenon Gas," Jour. of NIH Res., vol. 6, No. 12, pp. 42–44 (Dec. 1994).

Glover et al., Research Directions in MR Imaging[1], Radiology., vol. 207, pp. 289–295, (1998).

Happer et al., "An Optical Pumping Primer," Hyperfine Interactions, vol. 38, pp. 435–470 (1987).

Heil et al., "Very long nuclear relaxation times of spin polarized helium 3 in metal coated cells," Physics Letters A 201, pp. 337–343 (1995).

Hou, et al., "Optimization of Fast Acquisition Methods for Whole–Brain Relative Cerebral Blood Volume (rCBV) Mapping with Susceptibility Contrast Agents," J. Mag. Res. Imaging, vol. 9 pp. 233–239 (1999).

Hunt et al., "Nuclear Magnetic Resonance of $^{129}$Xe in Natural Xenon," Phys. Rev., vol. 130, p. 2302–2305 (Jun. 15, 1963).

Kaatz et al., "A comparison of molecular hyperpolarizabilities from gas and liquid," J. Chem. Phys., vol. 108, No. 3, pp. 849–856 (Jan. 15, 1998).

Kauczor et al., "Imaging of the Lungs Using 3He MRI: Preliminary Clinical Experience in 18 Patients with and without Lung Disease," JMRI, vol. 7, No. 3, pp. 538–543 (1997).

Kauczor et al., "MRI Using Hyperpolarized Nobel Gases," Eur. Radiol., vol. 8, No. 5, Abstract (1998).

Knudsen et al., "Blood–brain barrier permeability measurements by double–indicator method using intravenous injection," pp. H987–H999 (Jul. 1993).

Lassen, "Cerebral Transit of an Intravascular Tracer May Allow Measurement of Regional Blood Volume But Not Regional Blood Flow," 4 J. Cereb. Blood Flow and Metab. pp. 633–634 (1984).

Le Bihan, "Magnetic Resonance Imaging of Perfusion*," Mag. Reson. In Med., vol. 14, pp. 283–292 (1990).

Le Roux et al., "Gas Transport Properties of Surface Fluorinated Poly(vinyltrimethyl–silane) Filmes and Composite Membranes," J. Membrane Sci., vol. 90, pp. 55–68 (1994).

Lockhart et al., Absence of Abundant Binding Sites for Anesthetics in Rabbit Brain: An In Vivo NMR Study, Anesthesiology, vol. 73, p. 455 (1990).

Martin, "The Pharmacokinetics of Hyperpolarized Xenon: Implications for Cerebral MRI," Jour. Magn. Reson. Imag., vol. 7, No. 5, pp. 848–854 (Sep.–Oct. 1997).

McKim et al., "Evidence of xenon transport through the gramicidin channel: a $^{129}$Xe–NMR study," Biochimica et Biophysica Acta 1193, pp. 186–198 (1994).

Middleton et al., "MR Imaging With Hyperpolarized $^3$He Gas", Magnetic Resonance In Medicine, vol. 33, pp. 271–275 (1995).

Miller et al., "Xenon NMR: Chemical shifts of a general anesthetic common solvents, proteins, and membranes", Proc. of the Nat. Acad. of Sci. (USA), vol. 78, No. 8, pp. 4946–4949 (Aug. 1981).

Miller, "$^{129}$Xe NMR in Polymers," Rubber Chem. and Tech., vol. 66, p. 455 (1993).

Mohr et al., "Surface Fluorination of Composite Membranes. Part I. Transport Properties," J. of Membrane Sci., vol. 55, pp. 131–148 (1991).

Moschos, A. et al., "Communications Nuclear Magnetic Relaxation of Xenon–129 Dissolved in Organic Solvents," J. Mag. Reson., vol. 95, pp. 603–606 (1991).

Mugler, III et al. Gradient–echo MR Imaging, RSNA Categorical Course in Physics: The Basic Physics of MR Imaging[1], U. of VA Health Sci. Ctr., pp. 71–88 (1997).

Mugler, III et al., "MR Imaging and Spectroscopy Using Hyperpolarized 129Xe Gas: Preliminary Human Results," 37 Magn. Reson. in Med., vol. 37, No. 6, pp. 809–815 (1997).

Nacher et al., "Recent Results on Hyperpolarized $^3$He–$^4$He Liquid Mixtures," Czechoslovak J. of Phys., vol. 46 Suppl. S6, pp. 3025–3032 (1996).

Patyal, "Longitudinal Relaxation and Diffusion Measurements Using Magnetic Resonance Signals from Laser–Hyperpolarized $^{129}$Xe Nuclei," J. Magn. Reson., vol. 126, No. 1, pp. 58–65, May 1997.

Pauly, "Permeability and Diffusion Data," The Polymer Handbook, VI, pp. 435–449, 1989.

Pfeffer et al., "$^{129}$Xe gas NMR spectroscopy and imaging with a whole–body imager," J. Mag. Reson. Ser. A., vol. 108, No. 1, pp. 106–109 (May 1994).

Pollack, G.L. et al., "Solubility of xenon in liquid n–alkanes: Temperature dependence and thermodynamic functions," J. Chem. Phys., vol. 7, No. 6, pp. 3221–3229 (Sep. 15, 1982).

Pollack G.L. et al., "Solubility of xenon in liquid n–alkanois: Thermodynamic functions in simple polar liquids," J. Chem. Phys., 81 (7) pp. 3239–3246 (Oct. 1, 1984).

Raferty et al., "High–Field NMR of Adsorbed Xenon Polarized by Laser Pumping," Phys. Rev. Lett., vol. 66, No., pp. 584–587 (1991).

Raferty, D. et al., "NMR of optically pumped xenon thin films", Chem. Phys. Lett., vol. 191, No. 5, pp. 385–390 (Apr. 8, 1992).

Romalis et al., "Accurate $^3$He Polarimetry Using the Rb Zeeman Frequencey Shift Due to the Rb– $^3$He Spin–Exchange Collisions," Phys. Rev. A, vol. 58, No. 4, pp. 3004–3011 (Oct. 1998).

Rosen et al., "Perfusion Imaging by Nuclear Magnetic Resonance," Mag. Reson. Quart., vol. 5, No. 4, pp. 263–281 (1989).

Ruth et al., "Production of Nitrogen–Free, Hyperpolarized $^{129}$Xe Gas," Appl. Phys. B, vol. 68, pp. 93–97 (1999).

Saam et al., "Nuclear Relaxation of $^3$He in the Presence of $O_2$," Phys. Rev. A, vol. 52, pp. 862–865 (1995).

Saam et al., "Edge Enhancement Observed with Hyperpolarized $^3$HE," Chem. Phys. Ltrs., vol. 263, pp. 481–487 (1996).

Sauer et al., "Laser–Polarized Liquid Xenon", Chem. Phys. Lett., vol. 277, pp. 153–158 (Oct. 3, 1997).

Schad et al., "Hyperpolarized Gases—A New type of MR Contrast Agents?," Acta Radiologica 38, Suppl. 412, pp. 43–46 (1997).

Schaefer, S.R. et al., "Frequency shifts of the magnetic–resonance spectrum of mixtures of nuclear spin–polarized noble gases and vapors of spin–polarized alkali–metal atoms," Phys. Rev. A., vol. 39, No. 11, pp. 5613–5623 (1989).

Schmidt et al., "Diffusion Imaging with Hyperpolarized $^3$He Gas," Jour. Mag. Reson., vol. 129, pp. 184–187 (1997).

Schoenbom , B.P., "Binding of Xenon to Horse Haemoglobin," Nature, 208:760 (1965).

Simonsen et al., "CBF and CBV Measurements by USPIO Bolus Tracking: Reproducibility and Comparison with Gd–Based Values," J. of Mag. Reson. Imag., vol. 9, pp. 342–347 (1999).

Song et al., "Effects of Diffusion on Magnetic Resonance Imaging of Laser–Polarized Xenon Gas," Journ. Chem. Phys., vol. 108, No. 15, pp. 6233–6239 (Apr. 1998).

Susskind, H. et al., "Studies of Whole–Body Retention and Celarance of Inhaled Nobel Gases," Prog. Nucl. Med., 5:13 (1978).

Tilton, Jr., et al, "Nuclear Magnetic Resonance Studies of Xenon–129 with Myoglobin and Hemoglobin," Biochemistry, vol. 21, No. 26, pp. 6850–6857 (1982).

Wagshul, M.E., "Polarization of $^3$He by Spin Exchange with High Density Laser Optically Pumped Rb Vapor," Thesis, Department of Physics, Harvard University (Nov. 1991).

Wilcock, R.J. et al., "Solubilities of gases in liquids II. The solubilities of He, Ne, Ar, Kr, 02, $N_2$, Co, $Co_2$, $CH_4$, $CF_4$, and SF6 in n–octane 1–octanol, n–decane, and 1–decanol," J. Chem. Themodyn., 10:317 (1978).

Wu et al., "Experimental Studies of Wall Interactions of Adsorbed Spin–Polarized $^{131}$Xe Nuclei," Phys. Rev. A, vol. 42, No. 5 (Sep. 1, 1990).

Wyrwicz, A.M. et al., "Noninvasive Observations of Fluorinated Anesthetics in Rabbit Brain by Fluorine–19 Magnetic Resonance," Science 222:428 (1983).

Yen, W.M. et al., "Nuclear Magnetic Resonance of Xe129 in Solid and Liquid Xenon," Phys. Rev., 131:269 (1963).

Zeng et al., "Experimental determination of the rate constants for spin exchange between optically pumped K, Rb, and Cs atoms and $^{129}$Xe nuclei in alkali–metal—novel–gas van der Waals molecules," Physical Review A, vol. 31, No. 1, p. 260–278 (Jan. 1985).

PCT Int. Search Report for Int. Application No. PCT/US99/25434, date of mailing 14/04/2000.

Goodson et al., *In vivo NMR and MRI Using Injection Delivery of Laser–Polarized Xenon,* 94 Proc. Natl. Acad. Sci. USA, pp. 14725–14729 (1997).

Hagspiel et al., "Angiography Using Injection of Gaseous Hyperpolarized $^{129}$XE," (Jun. 2, 1999).

Möller et. al., *Magnetic Resonance Angiography with Hyperpolarized 129Xe Dissolved in Lipid Emulsion,* 41 Mag. Res. Med. No. 5, pp. 1058–1064 (1999).

Moseler et al, "Formation, Stability, and Breakup of Nanojets, Science," vol. 289, No. 5482, pp. 1165–1169 (Aug. 18, 2000).

van Blankenstein et al., *Cardiac Depression after Experimental Air Embolism in Pigs: Role of Addition of a Surface–Active Agent,* 34 Cardiovascular Research, pp. 473–482 (1997).

Wolber et al., *Perfluorocarbon Emulsions as Intravenous Delivery Media for Hyperpolarized Xenon,* 41 Mag. Res. Med., pp. 442–449 (1999).

\* cited by examiner

TO NMR APPARATUS

HYPERPOLARIZED HELIUM-3 MICROBUBBLE GAS ENTRAPMENT METHODS AND ASSOCIATED PRODUCTS

RELATED APPLICATIONS

This application is a divisional of U.S. application Ser. No. 09/428,814 filed Oct. 28, 1999, U.S. Pat. No. 6,284,222, which claims the benefit of priority from provisional U.S. Application Ser. No. 60/106,843, filed Nov. 3, 1998. The contents of these documents are hereby incorporated by reference as if recited in full herein.

FIELD OF THE INVENTION

The present invention relates generally to hyperpolarized Helium-3 ("$^3$He") and is particularly suitable for Magnetic Resonance Imaging ("MRI") and NMR spectroscopic medical diagnostic applications.

BACKGROUND OF THE INVENTION

Conventionally, MRI has been used to produce images by exciting the nuclei of hydrogen molecules (present in water protons) in the human body. However, it has recently been discovered that polarized noble gases can produce improved images of certain areas and regions of the body, which have heretofore produced less than satisfactory images in this modality. Polarized $^3$He and Xenon-129 ("$^{129}$Xe") have been found to be particularly suited for this purpose. Unfortunately, as will be discussed further below, the polarized state of the gases are sensitive to handling and environmental conditions and, undesirably, can decay from the polarized state relatively quickly.

"Polarization" or hyperpolarization of certain noble gas nuclei (such as $^{129}$Xe or $^3$He) over the natural or equilibrium levels, i.e., the Boltzmann polarization, is desirable because it enhances and increases MRI signal intensity, allowing physicians to obtain better images of the substance in the body. See U.S. Pat. No. 5,545,396 to Albert et al., the disclosure of which is hereby incorporated herein by reference as if recited in full herein.

For medical applications, after the hyperpolarized gas is produced, it is processed to form a non-toxic or sterile composition prior to introduction into a patient. Unfortunately, during and after collection, the hyperpolarized gas can deteriorate or decay (lose its hyperpolarized state) relatively quickly and therefore must be handled, collected, transported, and stored carefully. The "$T_1$" decay constant associated with the hyperpolarized gas' longitudinal relaxation time is often used to describe the length of time it takes a gas sample to depolarize in a given container. The handling of the hyperpolarized gas is critical, because of the sensitivity of the hyperpolarized state to environmental and handling factors and the potential for undesirable decay of the gas from its hyperpolarized state prior to the planned end use, i.e., delivery to a patient. Processing, transporting, and storing the hyperpolarized gases—as well as delivery of the gas to the patient or end user—can expose the hyperpolarized gases to various relaxation mechanisms such as magnetic gradients, ambient and contact impurities, and the like.

In the past, various hyperpolarized delivery modes such as injection and inhalation have been proposed to introduce the hyperpolarized gas to a patient. Inhalation of the hyperpolarized gas is typically preferred for lung or respiratory type images. To target other regions, other delivery paths and techniques can be employed. However, because helium is much less soluble than xenon in conventional carrier fluids such as lipids or blood, $^3$He has been used almost exclusively to image the lungs rather than other target regions.

Recent developments have proposed overcoming the low solubility problem of helium by using a micro-bubble suspension. See Chawla et al., *In vivo magnetic resonance vascular imaging using laser-polarized $^3$He microbubbles*, 95 Proc. Natl. Acad. Sci. USA, pp. 10832–10835 (September 1998). Chawla et al. suggests using radiographic contrast agents as the injection fluid to deliver microbubbles of hyperpolarized $^3$He gas in an injectable formulation. This formulation can then be injected into a patient in order to image the vascular system of a patient.

Generally stated, one way currently used to load or produce the microbubble mixture is via "passive" permeability. That is, the hyperpolarized $^3$He typically enters the walls of the micro-bubbles based on the helium permeability of the bubble itself. Thus, this gas loading method can take an undesirable amount of time, which can allow the hyperpolarized gas to decay unduly. Further, contact with the fluid or even the microbubble can result in contact-induced depolarization which can dominate the relaxation mechanisms of the hyperpolarized $^3$He and cause an undesirable reduction in the hyperpolarized life of the gas.

As such, there remains a need to improve micro-bubble $^3$He formulations and loading methods to minimize the decay of the polarized gas and improve the $T_1$ of the micro-bubble formulation.

In addition, there is also a need to increase the ease of solubilizing hyperpolarized gaseous xenon, which, in the past, has been problematic.

OBJECTS AND SUMMARY OF THE INVENTION

It is therefore an object of the present invention to improve the $T_1$ for a hyperpolarized $^3$He microbubble injectable solution.

It is another object of the present invention to reduce the effect of contact-induced depolarization to increase the hyperpolarized life of an injectable microbubble product.

It is an additional object of the present invention to produce an injectable microbubble solution in a way which increases the concentration of hyperpolarized $^3$He in the microbubbles in the injectable formulation.

It is another object of the invention to provide methods and devices for administering polarized microbubble injectable formulations to a subject in a manner which can rapidly mix and deliver the formulation to capitalize on the polarized state of the gas before it deleteriously decays.

It is another object of the present invention to process and form a hyperpolarized $^3$He gas mixture in improved containers and injection delivery systems which are configured to inhibit depolarization in the collected polarized gas.

It is yet another object of the invention to provide methods, surface materials and containers which will minimize the depolarizing effects of the hyperpolarized state of the $^3$He gas in a microbubble solution attributed to one or more of paramagnetic impurities, oxygen exposure, stray magnetic fields, and surface contact relaxation.

It is another object of the present invention to provide a dissolution assist method for facilitating the transition of hyperpolarized $^{129}$Xe from a gaseous to a liquid state.

These and other objects are satisfied by the present invention, which is directed to microbubble related hyperpolarized gas injectable solution (solubilized or liquid) products and related production and delivery methods, systems, and apparatus.

A first aspect of the present invention is directed to a method of producing an injectable formulation of hyperpolarized $^3$He. The method includes the steps of introducing a plurality of microbubbles into a chamber and then directing a quantity of hyperpolarized $^3$He into the chamber with the plurality of microbubbles. The pressure in the container is increased to above one atmosphere. A quantity of liquid is then directed into the chamber after the quantity of hyperpolarized gas and the microbubbles are located therein. The microbubbles with the (filled) hyperpolarized $^3$He contact the liquid thereby producing an injectable formulation of hyperpolarized $^3$He microbubbles.

In a preferred embodiment, the pressure is increased to above 2 atmospheres, and preferably increased to between about 2–10 atm. It is also preferred that the increasing step is performed after the microbubbles are introduced into the chamber and before the liquid is introduced therein.

Preferably, the liquid solution is selected such that it inhibits the depolarization of the gas based on contact with same. For example, in one embodiment, the fluid is selected such that it has low solubility values for $^3$He (preferably less than about 0.01, and more preferably less than about 0.005–0.008) or high diffusion coefficient value for $^3$He. In operation, the microbubble surface or walls are configured in the absence of the injection liquid to allow the hyperpolarized $^3$He to freely enter through the exterior cage-like shell of the bubble, then the fluid or liquid wraps around the openings in the cage-like shell to trap the hyperpolarized gas therein in such a way as to inhibit the transfer or leaching of the gas out of the microbubble. In addition, or alternatively, the fluid itself is introduced in a relatively limited quantity which can reduce the pressure differential between the $^3$He in the bubbles and those in the fluid and/or a quantity of $^3$He can be premixed with the liquid solution. The reduced pressure differential (saturation or equilibrium of the $^3$He in the fluid external of the bubbles) can reduce the amount of $^3$He which migrates therefrom.

In addition, even if the $^3$He exits the bubble, the low solubility of the selected fluid can reduce the amount of migration of helium from the bubble until equilibrium/saturation to prolong polarization associated therewith, thereby prolonging the $T_1$ of the microbubble injectable mixture. Indeed, the selection of the fluid will be an important factor in establishing a sufficiently long $T_1$ for the injectable formulation itself. Alternatively, or additionally, for formulations directed to $^3$He dissolved into liquid, it is preferred that the liquid have a high diffusion coefficient for $^3$He (high diffusion preferably meaning about $1.0 \times 10^{-5}$ cm$^2$/s and more preferably at least $1.0 \times 10^{-4}$ cm$^2$/s).

Another aspect of the present invention is directed toward a method of mixing and formulating polarized gaseous $^3$He for in vivo injection. The method includes the steps of introducing a quantity of microbubbles into a container and applying a vacuum to the container. The method also includes directing a first quantity of hyperpolarized $^3$He gas into the evacuated container with the microbubbles and directing a second quantity of a fluid into the container thereafter to form a bubble solution. The bubble solution is then removed from the container and injected into a subject.

Preferably, the second quantity of fluid comprises a substantially deoxygenated fluid and the injecting step includes delivering the bubble solution to an in situ positioned catheter inserted into the vein of a subject. It is also preferred that the mixing portion of the method be carried out temporally proximate to the injecting step (preferably performed within about 30 seconds prior to the injection).

An additional aspect of the present invention is directed toward a method of solubilizing gaseous hyperpolarized $^{129}$Xe. The method includes the steps of introducing a first quantity of bubbles into a chamber and directing a second quantity of hyperpolarized $^{129}$Xe into the chamber such that at least a portion of the $^{129}$Xe contacts the microbubbles. The method also includes the steps of dissolving a portion of the $^{129}$Xe and then separating substantially all of the microbubbles from the $^{129}$Xe prior to delivery of the dissolved phase of the 129Xe to a subject. The microbubbles act as an accelerant to solubilize the $^{129}$Xe from a gaseous state.

Yet another aspect of the present invention is a pharmaceutical injectable in vivo fluid hyperpolarized product. The product includes a first quantity of microbubbles formed from a first material and a second quantity of hyperpolarized $^3$He. The product also includes a third quantity of a liquid carrier solution. The third quantity is less than or substantially equal to the sum of the first and second quantities.

Preferably, the microbubbles are sized to be less than about 10 μm in diameter and the injectable product is single bolus sized as about 50 cc's.

The present invention includes methods to increase the density of the $^3$He in each microbubble (increasing the loading density) and to increase the bubble packing density to "pack" the bubbles more densely in the solution. Each can provide one or more of stronger signal strength and greater effective $T_1$'s.

Further, the present invention can allow reduced bolus sized quantities of $^3$He. For example, venous hyperpolarized gas microbubble injection volumes of from about 5–50 cc's, and more preferably about 15–30 cc's, can provide sufficient signal for clinically useful images. Preferably, the microbubble formulations of the present invention are also formed such that the gas microbubbles are sized to be less than about 10 μm and more preferably about 8 μm or less in diameter so as to be able to be injected in a venous side of the circulation system and then pass through the capillaries to the arterial side of the circulation system Advantageously, one or more of the loading of the gas into the bubble, and the delay in its escape, and the fluid packing and fluid compatibility can facilitate the delivery of quantities of the $^3$He in a manner which can allow the gas to be injected into a target area in a sufficient quantity and strength to provide clinically useful information.

The present invention, recognizing the very limited ($T_1$) life of the microbubble formulations, also provides a rapid mixing and delivery device which can allow the bubble mixing and formulation preparation temporally proximate to the point of injection (preferably injected via a catheter). The present invention also allows for an NMR coil to be positioned on and/or operably associated with the microbubble formulation (on the gas-filled bubble formulation holding chamber or associated conduits, catheters, or holding chamber stems and the like) to allow for a polarization measurement to be conveniently obtained in conjunction with a planned delivery to better calibrate the signal intensity and/or reduce the delivery of depolarized substances.

DETAILED DESCRIPTION OF THE INVENTION

Figure 1:
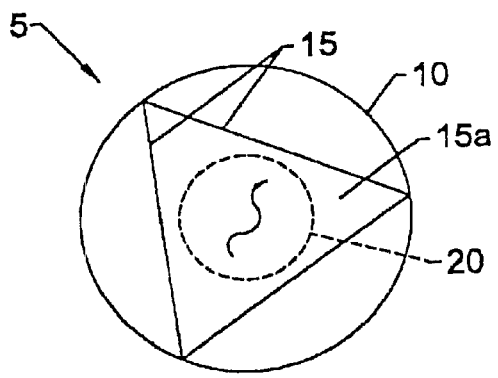
FIG. 1 schematically illustrates a microbubble cage-like shell (the specific configuration and size of the opening(s) in the "shell" being attributed to the molecular structure of the bubble material itself) and loading method according to the present invention.

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout. In the figures, certain features have been exaggerated for clarity or drawn for illustration purposes and as such the figures are not drawn to scale. For example, a typical microbubble is sized such that it is much larger (preferably sized at about 10 μm or less) than a 5 Å atom of $^3$He (e.g., about 2000 times larger). In addition, it will be appreciated that the molecular make-up of the bubble (corresponding to the particular bubble material(s)) will provide the specific configuration and size of the opening(s) and structure of the shell and walls and the figures herein are merely for schematic representation and discussion.

Background—Polarized Gas Relaxation Processes

Once hyperpolarized, there is a theoretical upper limit on the relaxation time ($T_1$) of the polarized gas based on the collisional relaxation explained by fundamental physics, i.e., the time it takes for a given sample to decay or depolarize due to collisions of the hyperpolarized gas atoms with each other absent other depolarizing factors. For example, $^3$He atoms relax through a dipole-dipole interaction during $^3$He—$^3$He collisions, while $^{129}$Xe atoms relax through N·I spin rotation interaction (where N is the molecular angular momentum and I designates nuclear spin rotation) during $^{129}$Xe—$^{129}$Xe collisions. Stated differently, the angular momentum associated with flipping over a nuclear spin is conserved by its being taken up by the rotational angular momentum of the colliding atoms. In any event, because both processes occur during noble gas-noble gas collisions, both resulting relaxation rates are directly proportional to gas pressure ($T_1$ is inversely proportional to pressure). Thus, at one atmosphere, the theoretical relaxation time ($T_1$) of $^3$He is about 744–760 hours, while for $^{129}$Xe the corresponding relaxation time is about 56 hours. See Newbury et al., *Gaseous $^3$He—$^3$He Magnetic Dipolar Spin Relaxation*, 48 Phys. Rev. A, No. 6, p. 4411 (1993); Hunt et al., *Nuclear Magnetic Resonance of $^{29}$Xe in Natural Xenon*, 130 Phys. Rev. p. 2302 (1963). Unfortunately, other relaxation processes prevent the realization of these theoretical relaxation times. For example, the collisions of gaseous $^{129}$Xe and $^3$He with container walls ("surface relaxation") have historically dominated most relaxation processes. For $^3$He, most of the known longer relaxation times have been achieved in special glass containers having a low permeability to helium. In the past, a fundamental understanding of surface relaxation mechanisms has been elusive, which has made the predictability of the associated $T_1$ difficult.

U.S. Pat. No. 5,612,103 to Driehuys et al. describes using coatings to inhibit the surface-induced nuclear spin relaxation of hyperpolarized noble gases, especially $^{129}$Xe. The disclosure of this patent is hereby incorporated by reference as if recited in full herein. Driehuys et al. recognized that nuclear spin relaxation of $^{129}$Xe on a polydimethoylsiloxane ("PDMS") surface coating can be dominated by dipolar coupling of the $^{129}$Xe nuclear spin to the protons in the polymer matrix. Thus, it was demonstrated that paramagnetic contaminants (such as the presence of paramagnetic molecules like oxygen) were not the dominant relaxation mechanism in that system because the inter-nuclear dipole-dipole relaxation was found to dominate the system under investigation. This was because $^{129}$Xe substantially dissolved into the particular polymer matrix (PDMS) under investigation. See Bastiaan Driehuys et al., *Surface Relaxation Mechanisms of Laser-Polarized $^{129}$Xe*, 74 Phys. Rev. Lett., No. 24, pp. 4943–4946 (1995).

Background—Relaxivity of Materials

In order to compare the characteristic information of certain materials concerning their respective relaxing effects on hyperpolarized noble gases, the term "relaxivity" is used. As used herein, the term "relaxivity" ("Y") is used to describe a material property associated with the rate of depolarization ("$1/T_1$") of the hyperpolarized gas sample. See co-pending and co-assigned U.S. patent application Ser. No. 09/126,448, entitled *Containers for Hyperpolarized Gases and Associated Methods*, the disclosure of which is hereby incorporated by reference as if fully recited herein.

Generally stated, gas dissolved in the polymer surface relaxes quickly (less than one second), so most of the hyperpolarized gas in the container is in the free gas form. Therefore, relaxation of this gas occurs through continual exchange between the free gas and the gas dissolved in the polymer. In material quantities, the rate of this gas exchange can be described by the "sorption parameters"—solubility ("S"), diffusion coefficient ("D"), and permeability ("P"). Permeability is the transmission of atoms or molecules through a (polymer) film. It depends on chemical and physical structure of the material as well the structure and physical characteristics of the permeant molecules. Permeability can be defined as the product of solubility and the diffusion coefficient ("P=S×D"). Solubility ("S") is a measure of how much permeant can be dissolved in a given material. Diffusion coefficient ("D") is a measure of the random mobility of the atoms in the polymer. Thus, the polymer sorption parameters can be used to characterize the relaxation of hyperpolarized gases in the presence of permeable surfaces.

As discussed in the above-referenced patent application, the relaxation rate ("$\Gamma_p$") in the polymer terms can be rewritten in terms of $T_1$, $\Gamma_p = 1/T_{1p}$. Solving for the relaxation time $T_1$:

$$T_1 = \frac{a}{S}\sqrt{\frac{T_1^p}{D_p}} \quad (1.00)$$

This analysis can be extended into three dimensions, yielding:

$$T_1 = \frac{V_c}{A_p S}\sqrt{\frac{T_1^p}{D_p}} \quad (1.10)$$

where $V_c$ is the internal volume of the chamber, $A_p$ is the exposed surface area of the polymer and S is the solubility of the gas in the polymer.

The inverse relationship between $T_1$ and S is a key observation from this development. There is also an apparent inverse square root dependence on the diffusion coefficient $D_p$. However, the relaxation time in the polymer $1/T_p$ also depends on $D_p$, canceling the overall effect on $T_1$. This leaves solubility as the dominant sorption characteristic in determining $T_1$.

$^3$He Microbubble Relaxation Considerations

The hyperpolarized $^3$He is introduced to at least three different contact related relaxation mechanisms when formulating the suspension mixture: the injection container related parameters such as the size, shape and material (as well as the materials of the proximately located seals and other components) of the container, the microbubble related parameters such as size, shape and material, and the injection fluid material. The container will be discussed further below but is preferably configured and formed from materials such that it is polarization-friendly.

Generally described, the microbubble acts as a miniature container to hold the hyperpolarized $^3$He. As such, the gas is preferably introduced into the "bubble" in a relaxation-efficient manner. Further, the structure of the microbubble is preferably such that the $^3$He can freely enter into the bubble through the exterior walls of the bubble in the absence of the injection liquid. Still further, the bubble is preferably loaded such that it retains increased amounts of $^3$He. The instant invention provides several alternatives of suitable material structure, and loading methods for the microbubble configurations in combination with different injection fluids and preferred associated material property values thereof as they relate to hyperpolarized $^3$He in order to optimize the microbubble injectable solution $T_1$.

In addition, it will be appreciated by one of skill in the art that the shell or wall thickness of the typical bubble is much thinner than the critical length scale $L_p$ (defined and discussed below). For example, for silicone, $D=4.1\ e^{-5}\ cm^2/s$ and $T_p=4.5$ s, and the associated length scale is about 100 $\mu$m. In contrast, the wall thickness of a typical bubble can be 5–6 orders of magnitude thinner (about 100 Å), thereby significantly reducing the role of the bubble wall in the depolarization analysis. Thus, the $T_1$ of the $^3$He gas in the bubble is not shorter than the $T_1$ of $^3$He in the fluid, i.e., it allows for increased or improved image acquisition time or more distal target imaging regions from the point of injection.

Loading

Assuming the microbubble is a spherical bubble of radius "R" and associated area ("A") of the shell with shell thickness "$\Delta x$" and that the initial volume of gas ($V_g$) which exists in the bubble shell is given by the product of gas solubility in the shell material (S), the gas density outside the shell $[G]_o$, and the volume of the shell ($\Delta x A$), then $$V_g = S[G]_o \Delta x A \quad (2)$$

The time it takes for this volume of gas to permeate through to the interior is limited by diffusion. Nominally, this time is given by $t=(\Delta x^2/D)$.

Thus, the volume of gas permeating into the shell per unit time can be expressed by:

$$\frac{d}{dt}V_g = \frac{S[G]_o DA}{\Delta x} \quad (3)$$

A more complex analysis may take into account the build-up of gas on the interior of the bubble and the resulting differential equation. As the interior gas concentration builds, the transfer of gas from the exterior will slow, and equilibrium will be reached in the form of a charging capacitor. However, a good working estimate of how long it takes to "load" the interior of the bubble with polarized $^3$He can be obtained without this analysis. This loading time can be described as $$\frac{d}{dt}V_g t_{load} = V \quad (4)$$

where (V) is the interior volume of the bubble. Thus, according to equation (5), estimates of hyperpolarized gas loading time into the bubble can be calculated as $$t_{load} = \frac{R\Delta x}{3S[G]_o D} \quad (5)$$

For example, assuming that $R=5\ \mu m=5\times10^{-4}$ cm and $[G]_o=1$ amagat and a helium solubility of $S \approx 0.01$ (which it typically is for most preferred materials), and using an estimate of a diffusion coefficient of helium in LDPE which is $D=6.8\times 10^{-6}$ cm$^2$/s and an extremely thin wall $\Delta x=100$ Å$=10^{-6}$ cm, the diffusion time is calculated as a reasonable $t \approx 2.5$ ms. For a larger wall thickness, on the order of $\Delta x=1\ \mu m=1.0\times10^{-4}$ cm, the loading time increases to 0.25 s, which, although slower, is still relatively good.

Increasing the Loading Density

Figure 2:
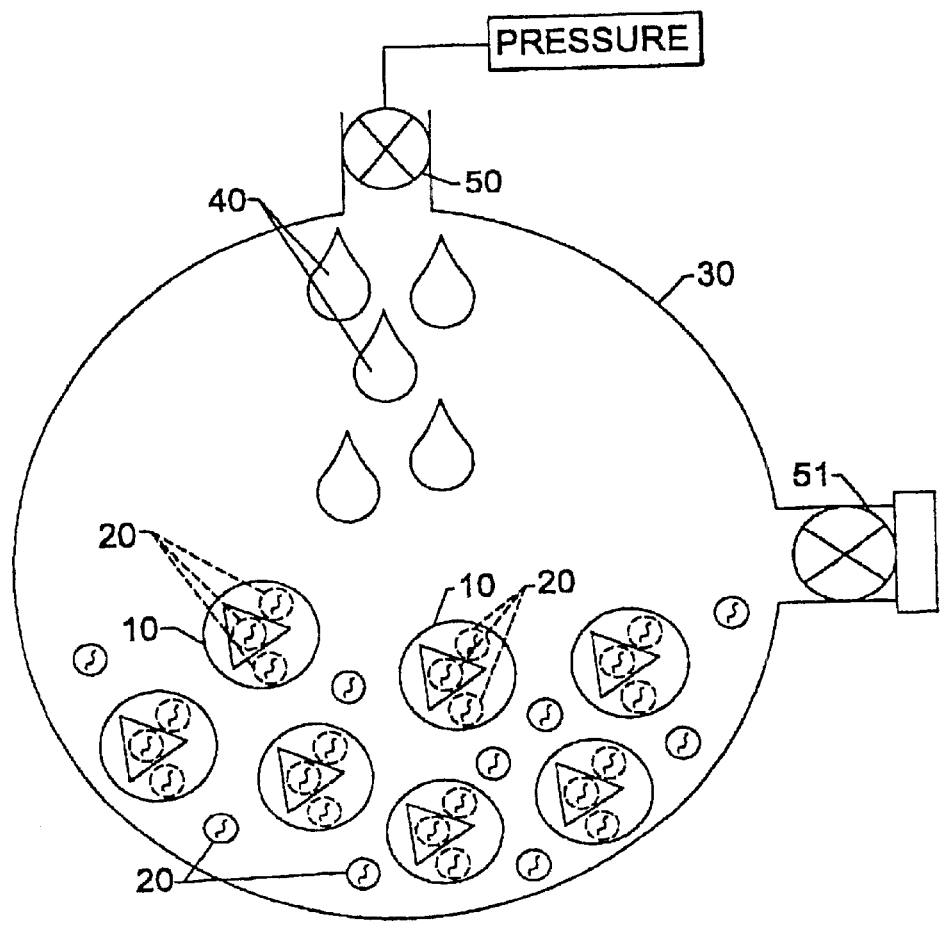
FIG. 2 schematically illustrates an apparatus or introduces a liquid into a microbubble and hyperpolarized $^3$He gas mixture.

As shown in FIG. 2, another way to increase the $T_1$ of the microbubble mixture is to increase the density or quantity of $^3$He loaded into the microbubble. This increased loading density can be attained by increasing the pressure in the preparation container to force additional quantities of $^3$He into a microbubble 10. The increased density of the polarized $^3$He in a microbubble 10 can prolong the effective $T_1$ of the solution. For example, escaped $^3$He can act to equilibrate the solution surrounding the microbubble thereby helping to retain partial quantities of the hyperpolarized $^3$He protected/isolated inside the bubble. Another advantage to increasing loading density is that increased quantities of $^3$He in the microbubbles can provide larger signal strength. Preferably, to load, the microbubble spheres are positioned in the container, the hyperpolarized gas is introduced via an air tight seal into the container and the pressure in the container 30 is increased above atmospheric pressure, preferably in the range of about 2–8 atm, and more preferably above 8 atm, and still more preferably up to about 10 atm, to create more densely packed bubbles.

Liquid Introduction

As will be appreciated by those of skill in the art, typically a microbubble which is structurally (at a molecular level) configured to allow the molecular $^3$He to enter will typically also just as easily allow it to leave. Thus, it is preferred that, once the hyperpolarized gas is inside the bubble, either the bubble and/or the liquid mixture acts to prevent or inhibit the gas from exiting from the interior of the bubble. In a preferred embodiment, the solution or mixture liquid is selected such that if the hyperpolarized gas does exit from the bubble, it contacts liquid which has a low solubility for the $^3$He, thereby limiting the total quantity of $^3$He which exits the bubble. "Low solubility" includes solutions selected such that they have a solubility for $^3$He ("S") which is less than about 0.01, and preferably less about 0.008, and more preferably less than about 0.005.

Alternatively, for solutions targeted at facilitating $^3$He dissolved in the mixture, the liquid can be selected such that the polarized $^3$He has a high diffusion coefficient therewith. Preferably, "high diffusion" means diffusion coefficient rates of above $1 \times 10^{-6}$ cm$^2$/s, and preferably more than about $6 \times 10^{-6}$ cm$^2$/s, and still more preferably above about $1.0 \times 10^{-5}$ cm$^2$/s, and even more preferably on the order of at least $1.0 \times 10^{-4}$ cm$^2$/s. Advantageously, a relatively long $T_1$ for the solution can be achieved for $^3$He dissolved in fluid by selecting a fluid which has a high diffusion coefficient for $^3$He.

The instant invention recognizes that the injection formulation of microbubbles can be improved by optimizing the microbubble structure itself to provide faster transport of the $^3$He therein. Preferably, the improved structure is provided by formulating a substantial quantity of the bubbles with a surface contact material which is selected to have a low solubility value for $^3$He. In an alternative embodiment, the microbubble material is selected such that it has a relatively thin wall and high diffusion coefficient value for $^3$He, which allows for the $^3$He to move into the bubble more rapidly.

Preferably, the bubbles are sized and configured with thin bubble wall thicknesses and miniaturized microbubble diameters. As used herein, "thin" means a bubble wall thickness of less than about 6 microns, and more preferably a wall thickness of about 1–2 microns. "Miniaturized" includes microbubble diameters which are less than about 10 microns, and preferably less than about 8 microns. The miniaturized size of the bubbles are particularly preferred for perfusion related images such that the bubbles are below about 8 microns so that they can freely travel into and/or through capillaries.

Figure 1A:
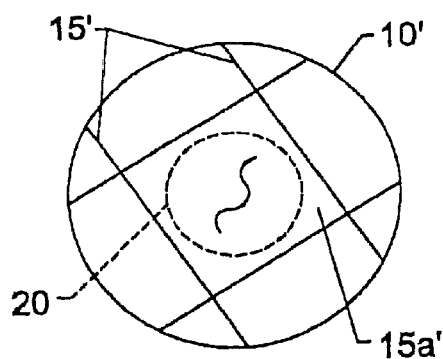
FIG. 1A schematically illustrates an alternative embodiment of a microbubble structure according to the present invention.

Referring to FIG. 1, one embodiment of the instant invention recognizes that a microbubble 10 can advantageously be formed from a material which is physiologically compatible and has a cage-like structure with walls 15 which can allow for quicker transport of the hyperpolarized gas 20 into the microbubble 10. The walls 15 of the microbubble define an opening 15a which is preferably sized such that it is slightly larger than the $^3$He. The $^3$He atom is on the order of about 2 Å–5 Å in diameter and thus the opening 15a in the wall of the microbubble is preferably larger than 2 Å. One alternative microbubble embodiment is schematically illustrated in FIG. 1A, in which a microbubble 10' has cage-like walls 15'.

In operation, as shown in FIG. 2, the $^3$He 20 and microbubbles 10 are positioned in a polarization friendly container and the hyperpolarized $^3$He 20 freely enters into the opening(s) 15a in the microbubble until a state of substantial equilibrium is reached. Preferably, the transport time (the time it takes the gas to enter the microbubbles) at increased pressure (above 1 atm) is below about 1 minute for a single dosage amount. That is, in a preferred embodiment, a quantity of microbubbles is introduced into a properly prepared and air tight sealed container (first). The pressure in the container is then elevated to above 1 atm, preferably to about 2–8 atm, and more preferably to above 8 atm, and still more preferably to about 10 atm. A quantity of polarized $^3$He gas is then subsequently directed into the container. The pressure facilitates the tendency of a portion of the hyperpolarized $^3$He to enter the bubble structure. Of course, the pressure can also be increased during the introduction of the $^3$He or even shortly thereafter (or ever prior to the introduction of the microbubbles, although not preferred). Preferably, the liquid is also injected into the container while the pressure is elevated. This liquid elevated pressure can be either at substantially the same pressure or a reduced elevated pressure from the microbubble/hyperpolarized gas loading pressure.

Figure 3:
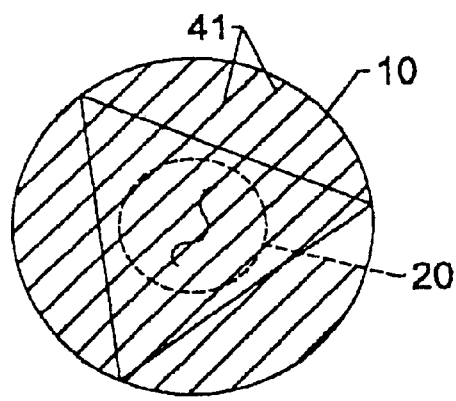
FIG. 3 schematically illustrates the liquid of FIG. 2 forming an outer wall or closing the cage-like opening(s) in the microbubble shell to trap the hyperpolarized gas therein.
Figure 4:
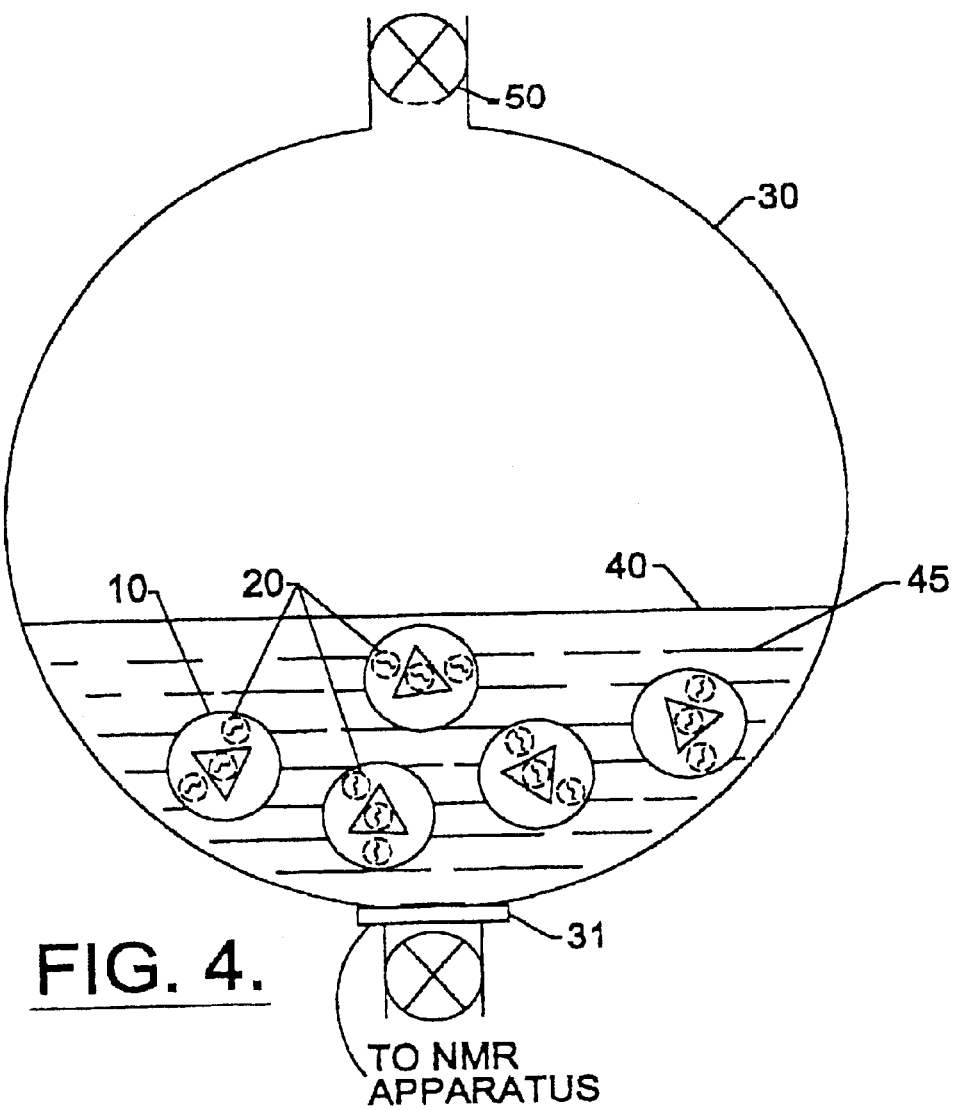
FIG. 4 schematically illustrates the microbubble mixture of FIG. 2 being withdrawn from the mixing container in preparation of injecting a predetermined amount into a target.

Also as shown in FIG. 2, after a predetermined (relatively short) transport time (typically less than about one minute as noted above, i.e., the time for at least a portion of the polarized $^3$He to move into the bubble structure), a liquid or fluid 40 is introduced into the container 30. In one preferred embodiment, it is preferred that the liquid 40 be selected such that the $^3$He has low solubility for the fluid ("S" less than about 0.01, and more preferably less than about 0.008, and still more preferably less than about 0.005). The low solubility helps inhibit polarization decay and preferably plugs the gaps or openings in the microbubble wall such that the $^3$He 20 is inhibited from leaving the microbubble. As shown in FIG. 4, the liquid 40 surrounds the microbubble and because the $^3$He is substantially insoluble in the fluid, the $^3$He 20 is repelled by contact with the liquid 40. Further, as shown in FIG. 3, the liquid forms the outer wall 41 of the microbubble 10, thus effectively "trapping" the $^3$He 20 in the microbubble. Of course, as noted above, the liquid can also be selected such that it has a high diffusion coefficient for the $^3$He. In any event, the $^3$He 20 and microbubbles 10 together with a solution or fluid mixture form an injectable formulation which preferably provides a single dose injectable volume which is about 5–50 cc's and preferably about 15–30 cc's.

Selection of the liquid introduced into the microbubble/hyperpolarized $^3$He combination is important. As discussed above, the liquid 40 is selected such that it provides a relatively long $T_1$ for the hyperpolarized gas as the gas may exit the microbubble or contact the fluid as it attempts to diffuse through the walls of the microbubble. For in vivo applications, it is preferred that the injection liquid be selected so as to be non-toxic and non-depolarizing to the hyperpolarized gas. Preferably, the liquid will be selected such that it has a low proton density along with the low solubility for $^3$He as noted above. Preferably, the proton density is less than or equal to about 125 mol/L, and more preferably less than about 120 mol/L, and still more preferably less than about 115 mol/L. It is further preferred, for liquids which have a relatively high oxygen solubility value, that the liquid be processed to be more compatible with the hyperpolarized gas. For example, it is preferred that the liquid be at least partially de-oxygenated and/or partially de-ionized prior to introduction into the container or transport vessel with the hyperpolarized gas. It is more preferred that the liquid be sterilized and substantially de-oxygenated and/or substantially de-ionized. Other modifications and treatment processes can also be performed on the liquids to make them more polarization-friendly. For example, certain elements of the liquids can be substituted or deuterated and the like.

Of course, a plurality of liquids can also be used as the fluid component, such as a liquid mixture or blend, whether miscible or immiscible. Tests indicate that water is a suitable liquid (preferably deoxygenated), as well as $D_2O$. Water is compatible and substantially non-depolarizing to $^3He$. Other liquid carriers are known such as those described in PCT/US97/05166 to Pines et al.

Previously, as noted in co-pending and co-assigned U.S. patent application Ser. No. 09/163,721, entitled *Hyperpolarized Noble Gas Extraction Methods, Masking Methods, And Associated Transport Containers*, adding about 20 cubic centimeters of partially degassed water into the chamber of a 250 ml container changed the associated $T_1$ of the gas in the container from about 8 hours to about 5 hours. The contents of this application is hereby incorporated by reference as if recited in full herein.

For a microbubble mixture comprising deoxygenated water as the filler wall 41, an estimation of the $T_1$ of the $^3He$ in such a microbubble mixture can be described by equation 1.10. For the estimation, an estimate of the solubility of helium and the density of protons in the fluid is established. The solubility of helium in water as stated by Weathersby et al., in *Solubility of inert gases in biological fluids and tissues*, Undersea Biomedical Research 7(4), 277–296 (1980), is given as 0.0098. The proton density of water is 111 mol/L (compared to 131.4 for LDPE). Thus, the ratio of water relaxivity to LDPE relaxivity is $(0.0098/0.006)(111/131)^{1/2}=1.5$. Knowing that the LDPE relaxivity is about 0.0012 cm/min, the water relaxivity value is about 0.0018 cm/min. Thus, to obtain an estimate of $T_1$, the volume of the bubble is divided by the surface area. For an 8 micron bubble, the V/A is about $2.7 \times 10^{-4}$ cm and $T_1$ is about 0.15 min (9 seconds). Doubling the diameter of the bubble to 16 micrometers can increase the time to 18 seconds. Using $D_2O$ as the fluid can provide a $T_1$ of about 36 seconds.

Figure 6:
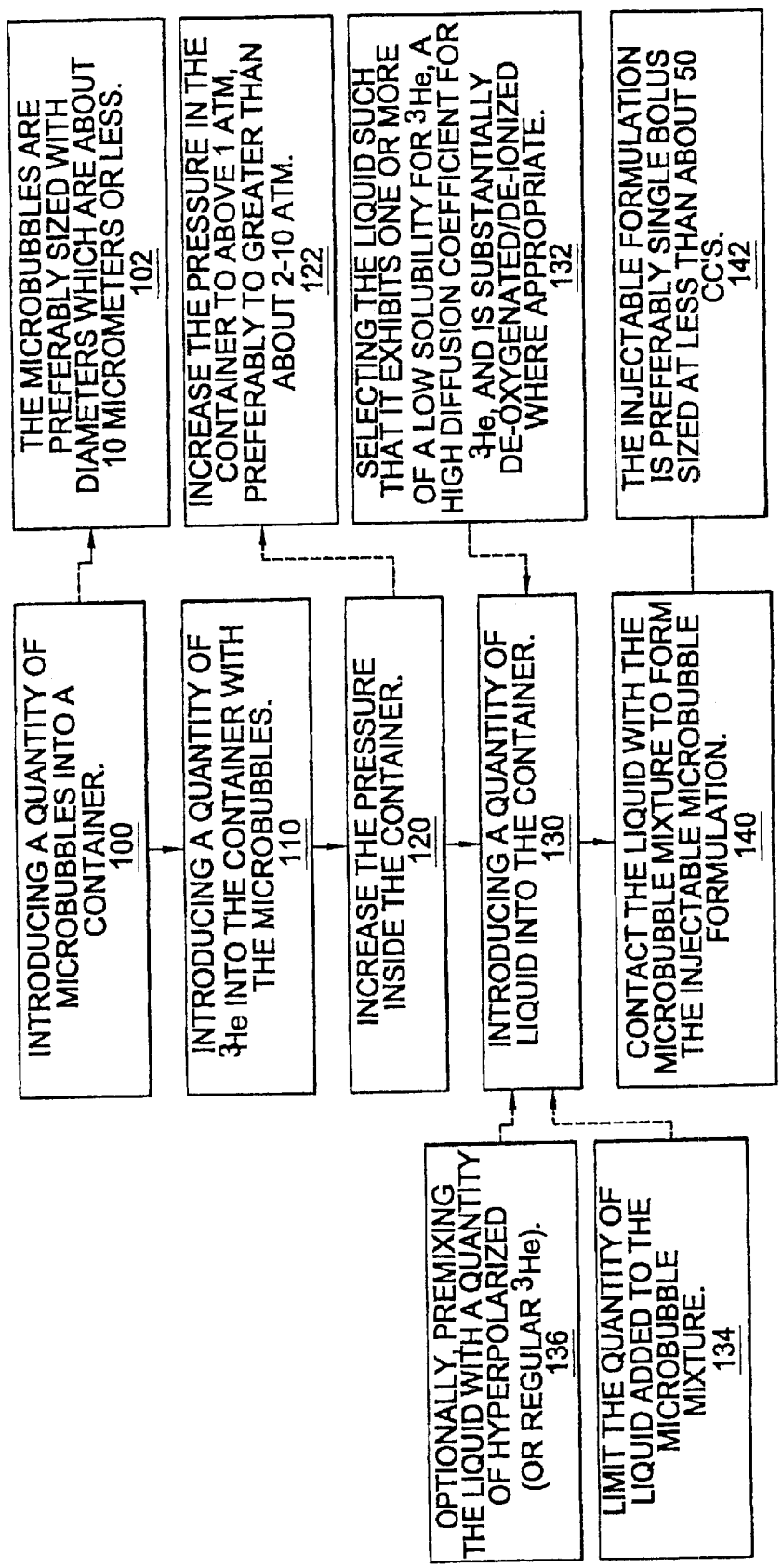
FIG. 6 is a block diagram of a method of formulating a microbubble injectable product.

FIG. 6 is a block diagram of the preferred method of forming an injectable $^3He$ microbubble solution. A quantity of microbubbles is introduced into a container (or gas holding chamber) (Block 100). Preferably the microbubbles are sized with a diameter which is about 10 μm or less (Block 102). Next, a quantity of hyperpolarized $^3He$ gas is introduced into the container (Block 110). The pressure in the container is increased to above atmospheric pressure (Block 120), preferably to between 2–10 atmospheres of pressure (Block 122). Of course, the pressure can be increased before the $^3He$ is introduced or, more preferably, subsequent to or concurrently with the introduction of the $^3He$ into the container.

The liquid (or liquid solution or mixture) is then introduced into the container (Block 130), preferably after a predetermined lapsed "transit" time. Preferably, the liquid is pre-selected to have one or more of low solubility for $^3He$, a high diffusion coefficient for $^3He$, and, where appropriate to be substantially de-oxygenated and/or de-ionized (Block 132). The liquid can be limited in quantity (Block 134) and/or premixed with another quantity of hyperpolarized gas (Block 136). The liquid, and the microbubble/$^3He$ then combine or reside together to form the injectable microbubble formulation (Block 140). Preferably, the injectable formulation is sized in a deliverable bolus of less than or equal to about 50 cc's (Block 142).

Bubble Packing

It is preferred that the amount of liquid introduced into the chamber with the microbubble/$^3He$ mixture be restricted to an amount about equal to or less than the volume of the combined volumes of $^3He$ and microbubbles in order to pack the $^3He$ within the "loaded" microbubble. As liquid volume decreases, signal strength based on same can increase and less dilution of ambient $^3He$ makes solubility appear smaller. For example, a 2 to 1 or 1 to 1 liquid to gas/microbubbles ratio or less, i.e., 20 cc's of microbubbles, 40 cc's $^3He$, and 60 cc's of liquid will provide a 1—1 ratio.

Alternatively, or additionally, increased quantities of polarized $^3He$ can be initially added to the liquid (premixed) to inhibit the tendency of the $^3He$ to migrate from the bubbles by providing at least residual amounts of $^3He$ within the liquid itself. This can build up the quantity in the solution and reduce leaching from the microbubbles. This additional or "surplus" $^3He$ can be added to the liquid before or concurrently with the liquid's introduction into the microbubble mixture in the container. For example, for a mixture comprising about 20 cc's of microbubbles, 20 cc's of gas, and a liquid in an amount less than about 40 cc's, a 20 cc amount of $^3He$ can be introduced to the liquid (prior to introduction into the container) to form the combined pre-mix liquid which is then directed into the chamber with the $^3He$ and microbubbles.

Stated differently, the instant invention recognizes that the $T_1$ of the solution is sensitive to bubble dilution in the liquid. Minimizing the liquid introduced into the mixture can minimize the equilibrium differential in the liquid mixture, which, in turn, should reduce the amount of depolarization occurring due to the leaching action. As such, a larger fraction of the $^3He$ will remain within the bubble. Saturation corresponds to solubility, which is a volume/volume measurement of about 0.01 according to the present invention Alternatively, or additionally, adding a liquid with previously introduced quantities of helium gas (i.e., the premix solution) can also reduce the partial pressure difference in the combined mixture, which can also facilitate a larger fraction of the $^3He$ to remain within the bubble.

These "bubble-packing" methods, particularly when used with a low-solubility liquid, can result in a higher $T_1$ formulation. In addition, using deuterated water for the solvent or liquid (or as a component thereof) can also help increase the $T_1$.

Due to the relatively short efficacy life of the injectable microbubble $^3He$ formulation, it is preferred that a rapid mixing and delivery system be employed to administer the formulation to a subject temporally related to initiation of the imaging sequence. That is, the pharmaceutical grade in vivo microbubble formulation is mixed onsite, temporally and physically proximate to or related to the point of injection, preferably mixed within about 30 seconds from the time of injection, and more preferably, rapidly and effectively mixed within about 10 seconds from the time of injection.

In any event, in operation, a measurement is preferably taken in advance or concurrently with the injection via a NMR coil 31 on the injection container or delivery path (conduit, syringe body, etc.) to affirm/determine the polarization level of the solution to allow the signal intensity to be correlated with the polarized level of the hyperpolarized solution which is delivered.

As shown in FIG. 4, the injection mixture 45 is withdrawn from the mixing chamber/transport container 30 into a syringe 70 (FIG. 5B) which is positioned in a port or septum operably associated with the valve 50 on the bottom of the container so that the liquid restricted mixture can be easily removed (with the help of gravity). Valves 50, 51 are also employed to control the pressure of the container. Typical valves include Luer Lok™ valves, glass valves such as those available from Konte Kimbles™, and polymer material valves can also be used as is known by those of skill in the art. Of course, other extraction methods and devices can also be used, such as those described in the co-pending and co-assigned patent application discussed above. Preferably, the syringe 70 and any O-rings and valves positioned proximate thereto are formed from or coated with materials (at least the gas contacting surfaces) which are polarization-friendly as will be discussed further below. Further, the containers and syringes and other gas contacting devices are preferably prepared to remove paramagnetic and magnetic impurities and oxygen and the like as will also be discussed further below. In addition, capillary stems and other separation or isolation means can be employed to separate potentially depolarizing valve members from the polarized gas as is discussed in co-pending and co-assigned U.S. patent application Ser. No. 09/334,400, the contents of which are hereby incorporated by reference as if recited in full herein.

Vacuum-Based Methods

Figure 5A:
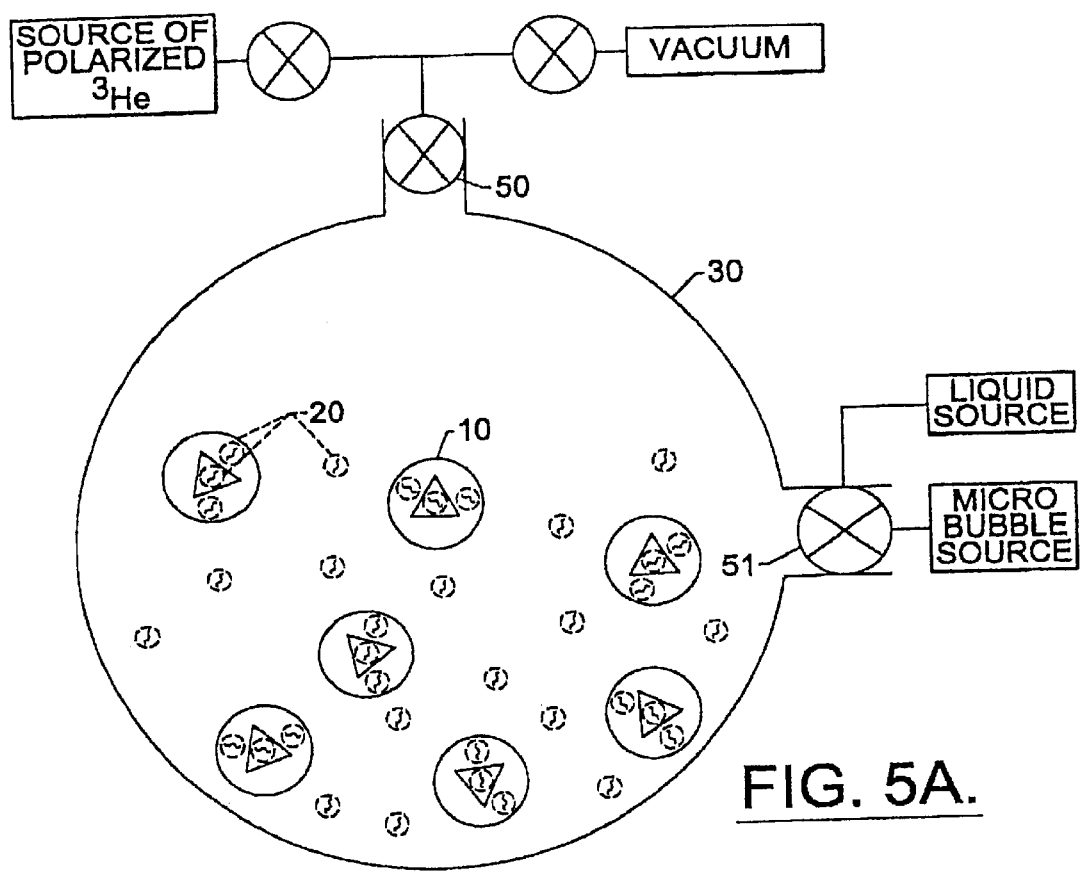
FIG. 5A is a front view schematic illustration of an evacuated delivery and mixing system.
Figure 5B:
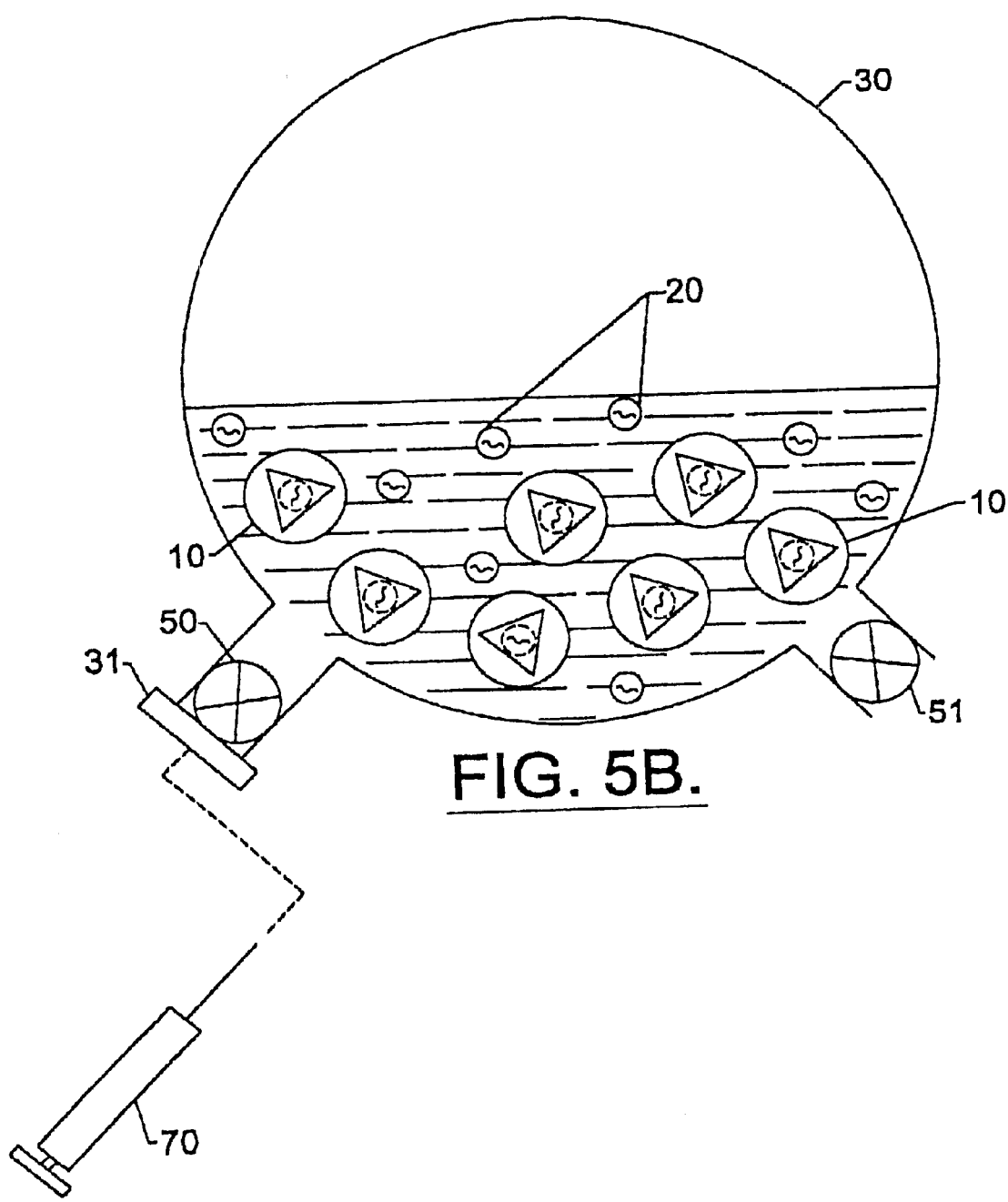
FIG. 5B is a front view schematic illustration of FIG. 5A showing a syringe (the syringe and container are shown exaggerated in scale for ease of representation) withdrawal and injectable delivery technique.

In an alternative microbubble fabrication method, a vacuum type microbubble formulation method is employed. Referring to FIGS. 5A and 5B, a quantity of microbubble shells 10 can be introduced under vacuum to an evacuated (cleaned/prepared) container 30. A quantity of gaseous $^3$He 20 can be directed into the container (the vacuum pulls the gas into the container). The evacuated state of the microbubbles induces the $^3$He gas to rapidly enter and/or fill the microbubble shells. Next, a sub-container 70 such as a syringe which is pre-filled with a liquid carrier solution (such as deoxygenated fluid, liquid, or water) can be injected into the container 30. The container 30 can be re-oriented to allow the subcontainer such as a syringe 70 to be backfilled with (preferably saturated) the bubble/polarized $^3$He/liquid solution. As shown in FIG. 5B, the backfilled syringe can then be detached and inserted into a catheter positioned in the subject. Alternatively, a LUER LOK™ valve system can be operated to direct the solution down conduit into the catheter and thereby injected. In operation, the vacuum is preferably pulled to at least 50 microns (millitorr), and more preferably to at least 10 microns. Thus, the evacuated method also allows for a relatively rapid or fast mix and delivery system.

Containers

Preferred materials for containers include aluminosilicates such as Pyrex® or hyperpolarized gas contacting surfaces formed of materials including non-magnetic high-purity metal films, high-purity metal oxides, high purity insulators or semi-conductors (such as high purity silicon) and polymers. As used herein, "high purity" includes materials which have less than about 1 ppm ferrous or paramagnetic impurities and more preferably less than about 1 ppb ferrous or paramagnetic impurities. Preferred polymers for use in the containers described herein include materials which have a reduced solubility for the hyperpolarized gas. For the purposes of the inventions herein, the term "polymer" is to be broadly construed to include homopolymers, copolymers, terpolymers and the like and should also include blends and mixtures thereof. The terms "blends and mixtures thereof" include both immiscible and miscible blends and mixtures. Examples of suitable materials include, but are not limited to, polyolefins (e.g., polyethylenes, polypropylenes), polystyrenes, polymethacrylates, polyvinyls, polydienes, polyesters, polycarbonates, polyamides, polyimides, polynitriles, cellulose, cellulose derivatives and blends and mixtures thereof. It is more preferred that the coating or surface of the container comprise a high-density polyethylene, polypropylene of about 50% crystallinity, polyvinylchloride, polyvinylflouride, polyamide, polyimide, or cellulose and blends and mixtures thereof. See also co-pending and co-assigned U.S. patent application Ser. No. 09/334,400, the contents of which are hereby incorporated by reference as if recited in full herein.

Of course, the polymers can be modified. For example, using halogen as a substituent or putting the polymer in deuterated (or partially deuterated) form (replacement of hydrogen protons with deuterons) can reduce the relaxation rate. Methods of deuterating polymers are known in the art. For example, the deuteration of hydrocarbon polymers is described in U.S. Pat. Nos. 3,657,363, 3,966,781, and 4,914,160, the disclosures of which are hereby incorporated by reference herein. Typically, these methods use catalytic substitution of deuterons for protons. Preferred deuterated hydrocarbon polymers and copolymers include deuterated paraffins, polyolefins, and the like. Such polymers and copolymers and the like may also be cross-linked according to known methods.

It is further preferred that the polymer be substantially free of paramagnetic contaminants or impurities such as color centers, free electrons, colorants, other degrading fillers and the like. Any plasticizers or fillers used should be chosen to minimize magnetic impurities contacting or positioned proximate to the hyperpolarized noble gas.

Alternately, in another embodiment, the contact surface can be formed from a high purity metal. The high purity metal can provide advantageously low relaxivity/depolarization resistant surfaces relative to hyperpolarized noble gases.

As noted above, any of these materials can be provided as a surface coating on an underlying substrate or formed as a material layer to define a friendly contact surface. If used as a coating, the coating can be applied by any number of techniques as will be appreciated by those of skill in the art (e.g., by solution coating, chemical vapor deposition, fusion bonding, powder sintering and the like). Hydrocarbon grease can also be used as a coating. The storage vessel or container can be rigid or resilient. Rigid containers can be formed of Pyrex™ glass, aluminum, plastic, PVC or the like. Resilient vessels are preferably formed as collapsible bags, such as collapsible polymer or metal film bags. Examples of materials which can provide oxygen resistance as well as low solubility include but are not limited to PET (polyethylene terphthalate), PVDC (polyvinylidene dichloride), Tedlar™ (polyvinylfluoride), cellophane and polyacrylonitrile.

Preferably, care is taken to insure that all fittings, seals, and the like which contact the hyperpolarized gas or which are located relatively near thereto are manufactured from materials which are friendly to polarization or which do not substantially degrade the polarized state of the hyperpolarized gas. For example, as noted above, many commercially available seals include fluoropolymers or fillers and the like which are not particularly good for the preservation of $^3$He hyperpolarized gases because of the solubility of the material with the hyperpolarized gas.

Inasmuch as many common gasket materials are fluoropolymers or contain undesirable fillers, they can potentially have a substantially depolarizing effect on the gas. This can be especially acute with respect to $^3$He. This can be attributed to a relatively high solubility of helium in most fluoropolymers due to the larger void space in the polymer attributable to the large fluorine atoms. Indeed, preliminary tests indicate that materials of common O-rings (such as Viton™, Kel-F™, ethylene-propylene, Buna-N™, and silicone) exhibit far worse relaxation properties than would be expected from the relaxation rate of pure polymers. Most conventional O-rings are so depolarizing that they can dominate the relaxation of an entire hyperpolarized gas chamber. Indeed, commercial ethylene propylene O-rings exhibit ⅓–½ the relaxation time compared to pure LDPE with $^{129}$Xe. The faster relaxation rate can be explained because magnetic impurities in the O-rings can be introduced by such things as colorants and fillers and the like. Therefore, it is preferred that the containers of the present invention employ seals, O-rings, gaskets and the like with substantially pure (substantially without magnetic impurities) hydrocarbon materials such as those containing polyolefins. Examples of suitable polyolefins include polyethylene, polypropylene, copolymers and blends thereof which have been modified to minimize the amount of magnetically impure fillers used therein. Additional suitable seals include hydrocarbon grease and hydrocarbon gaskets and O-rings made from polyethylene and the like. Thus, if a valve is used to contain the gas in the chamber 30, it is preferably configured with reduced magnetic impurities (at least the surface) O-ring and/or with hydrocarbon grease. Of course, because fillers and plasticizers are employed, then it is preferred that they be selected to minimize the magnetic impurities, one preferred material being substantially pure carbon black.

In an alternative embodiment, the O-ring seal can be configured with the exposed surface coated with a high purity metal as discussed for the container surface. Similarly, the O-ring or seal can be coated or formed with an outer exposed layer of a polymer at least "$L_p$" thick. For example, a layer of pure polyethylene can be positioned over a commercially available O-ring. One preferred commercially available O-ring material for $^{129}$Xe is a Teflon™ coated rubber O-ring or a low-relaxivity polymer as discussed above. The void spaces in Teflon™ (although it is a fluoropolymer) do not affect $^{129}$Xe as much as they do $^3$He because $^{129}$Xe is much larger than fluorine, which is much larger than $^3$He. As discussed previously, fluoropolymers can be used as seals with $^{129}$Xe but are not preferable for use with arrangements where the seal may contact the hyperpolarized $^3$He.

In order to determine the "$L_p$" thickness, wherein the layer thickness ("$L_{th}$") is at least as thick as the polarization decay length scale ("$L_p$"), one can calculate or determine the thickness for a particular material type according to the equation:

$$L_p = \sqrt{T_p D_p} \qquad (6)$$

where $T_p$ is the noble gas nuclear spin relaxation time in the polymer and $D_p$ is the noble gas diffusion coefficient in the polymer. For example, a layer of substantially pure polyethylene can be positioned over a commercially available O-ring. Alternatively, the O-ring or seal can be coated with a surface material such as LDPE or deuterated HDPE or other low-relaxivity property material. It is also preferred that the relaxivity value "Y" is less than about 0.0012 cm/min for $^3$He.

When bags with long surface relaxation times are used as containers, other relaxation mechanisms can become important. One of the most important additional relaxation mechanisms is due to collisions of the noble gas with paramagnetic oxygen. Because $O_2$ has a magnetic moment, it can relax hyperpolarized gases in the same manner as protons. Given this problem, care should be taken to reduce the oxygen content in the storage container through careful preconditioning of the container, such as by repeated evacuation and pure gas purging procedures. Preferably, the container is processed such that the $O_2$ concentration yields a $T_1$ of about 1000 hours or more. More preferably, the container is processed to obtain an $O_2$ concentration on the order of about $6.3 \times 10^{-6}$ atm or less or about $10^{-7}$ atm or less, and even more preferably less than about $1 \times 10^{-10}$ atm. Additionally, the evacuation/purge procedures can include heating the container or other evacuating or pumping methods to additionally facilitate the removal of any remaining (monolayer) residual amounts of moisture or water.

Preferably, the mixing container/interfaces, syringes, and tubing are prepared in advance of use to minimize any preparation required at the time of use at the gas injection site. Therefore, preferred pre-conditioning or equipment preparation methods such as cleaning, evacuating, and purging the components to remove oxygen and paramagnetic contaminants are preferably done off-site. After preparation/conditioning, the pre-conditioned syringes can be stored at the hospital for use under pressure with a noble gas or benign liquid therein. This pre-filled gas or fluid storage can minimize the potential for the containers, syringes or components to degas (gas from the matrix of a material such as oxygen can migrate into the chamber onto the contact surfaces), and can also minimize air leaking into the container. Alternatively, or in addition to the pre-conditioning, the pressurized tubing and delivery vessels (and/or syringes) can be sealed with check valves or other valved ports. In another alternative, vacuum tight valves can allow the tubes and containers to be stored for use under vacuum rather than under positive pressure.

The hyperpolarized gas is collected (as well as stored, transported, and preferably delivered) in the presence of a magnetic field. For $^3$He, the magnetic field is preferably on the order of at least 5–30 gauss although, again, higher (homogeneous) fields can be used. The magnetic field can be provided by electrical or permanent magnets. In one embodiment, the magnetic field is provided by a plurality of permanent magnets positioned about a magnetic yoke which is positioned adjacent the collected hyperpolarized gas. Preferably, the magnetic field is homogeneously maintained around the hyperpolarized gas to minimize field induced degradation.

In operation, the injected hyperpolarized $^3$He of the present invention can provide signal strengths even in relatively small quantities which can be detected by known NMR spectroscopy and imaging methods. In a preferred embodiment, a second quantity of $^3$He is delivered via inhalation to allow both a perfusion (injection based) and ventilation (inhalation based) MR image or "VQ scan". Because $^3$He is used for both excitations/data acquisition, for vasculature images, a single NMR excitation coil (chest coil) can be conveniently used to obtain both signals.

Dissolving Xenon

In addition, microbubbles can be used as a dissolving mechanism to assist in dissolving xenon into a liquid, which has traditionally been extremely reluctant to dissolve into a carrier liquid. As an example, a vial with a plurality of microbubbles is provided. Next, polarized $^{129}$Xe is added to the vial. A solvent or liquid mixture (preferably physiologically compatible and non-toxic and sterile) is added to provide an optimal bubble packing fraction (i.e., a limited amount of liquid as discussed above). Alternatively, the amount of liquid can be increased to provide a diluted liquid mixture, thus inducing the xenon to exit the bubble to achieve equilibrium. In any event, the xenon rapidly leaches into the solution out of the microbubble. Preferably, prior to injection, the bubbles are strained or filtered out leaving a liquid with dissolved xenon. Advantageously, the microbubbles can then act as an accelerant to assist in the xenon dissolving in a liquid, which, in the past has been time consuming and problematic.

Of course, because the microbubbles will preferably be filtered from the dissolved xenon, the microbubble size is not limited by the injection thereof into in vivo systems. Exemplary compatible fluids are described in PCT/US97/05166 to Pines et al.

Drug Evaluations

Although it is preferred that the microbubble injectable formulation be a pharmaceutical grade in vivo formulation (such as a non-toxic and sterilized solution, with the alkali metal separated from the hyperpolarized gas according to FDA standards(for alkali spin exchange hyperpolarized gases), the present invention is not limited thereto. Indeed, rapid advances are being made with the ability to treat and target many diseases with innovative drug and drug therapies. NMR spectroscopy based on hyperpolarized gases can be used to observe the effects of administered drugs on the biochemistry of the organism or the changes in the drug which occur following its administration. The instant invention can allow for improved sensitivity and potentially higher resolution information for evaluations of the treatments or even the chemical processes underlying a disease state with respect to the desired target tissues or organs within the body. For example, delivery of the injectable microbubble solution to an animal or in vitro target can evaluate the efficacy of treatment on function or the progression or regression/improvement of a condition in the pulmonary vasculature, cardiac, brain, or other tissue, organ, or system.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clauses are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included.

That which is claimed is:

1. A method of preparing and subsequently injecting polarized gaseous $^3$He in vivo, comprising the steps of:
   (a) introducing a quantity of microbubbles into a container;
   (b) applying a vacuum to the container;
   (c) directing a first quantity of hyperpolarized $^3$He gas into the evacuated container with the microbubbles;
   (d) directing a second quantity of a fluid into the container to form a bubble solution after the first directing step; and
   (e) injecting the bubble solution into a subject.

2. A method according to claim 1, wherein the second quantity of fluid comprises a substantially deoxygenated fluid.

3. A method according to claim 1, wherein said injecting step includes delivering the bubble solution to a catheter inserted into the vein of a subject.

4. A method according to claim 1, wherein steps (b) through (d) are carried out temporally proximate to step (e).

5. A method according to claim 1, wherein steps (b) through (e) are carried out in less than about 30 seconds.

6. A method according to claim 1, further comprising the step of acquiring NMR signal data based on the detection of the hyperpolarized gas delivered to a target via the bubble solution.

7. A method according to claim 1, wherein the second quantity of fluid is a liquid.

8. A method according to claim 7, wherein the bubble solution is an injectable formulation which is physiologically compatible.

9. A method according to claim 7, wherein the liquid is nontoxic and sterile.

10. A method according to claim 7, wherein the liquid is added in an amount which is greater than the combined volumes of microbubbles and gaseous $^3$He.

11. A method according to claim 1, wherein the chamber is held in an evacuated state while the microbubbles are directed therein.

12. A method according to claim 11, the chamber remains in an evacuated state while the polarized $^3$He is directed therein.

13. A method according to claim 1, wherein said applying step decreases the pressure in the chamber to less than about 50 microns (millitorr).

14. A method according to claim 13, wherein the pressure is decreased in the chamber to at least about 10 microns.

15. A method of preparing polarized gaseous $^3$He, comprising the steps of:
   (a) evacuating a container;
   (b) introducing a quantity of microbubbles into the evacuated container;
   (c) directing a first quantity of hyperpolarized $^3$He gas into the evacuated container with the microbubbles after the microbubbles are introduced in the evacuated container; and
   (d) subsequently directing a second quantity of a fluid into the container to form a bubble solution.

16. A method according to claim 15, wherein the second quantity of fluid is a substantially deoxygenated liquid.

17. A method according to claim 15, wherein said bubble solution is a biocompatible injectable formulation for in vivo administration.

18. A method according to claim 15, wherein the bubble solution is formulated for delivery to an in vitro target.

19. A method according to claim 13, further comprising the steps of delivering the bubble solution to a target and acquiring NMR signal data based on the detection of the hyperpolarized gas delivered to a target via the bubble solution.

20. A method according to claim 16, wherein the liquid is substantially deoxygenated water.

21. A method according to claim 15, wherein the second quantity of fluid is a liquid which is substantially de-ionized.

22. A method according to claim 15, wherein the second quantity of fluid is a liquid which comprises an increased concentration of $D_2O$ relative to that naturally found in water.

23. A method according to claim 15, wherein the fluid is a liquid that has a low proton density.

24. A method according to claim 15, wherein the microbubble material has a high diffusion coefficient for $^3He$.

25. A method according to claim 15, further comprising the steps of injecting the bubble solution into a biological subject and measuring the polarization level of the $^3He$ proximate in time to said injecting step, said step of directing the hyperpolarized $^3He$ into the evacuated container is carried out temporally proximate to said injecting step.

26. A method according to claim 15, wherein the bubble solution is an injectable formulation which is sized in the range of over 7 cc's and at or below about 50 cc's.

27. A method according to claim 15, further comprising the step of measuring the polarization of the bubble solution post-formulation and proximate to delivery to a target to determine level of polarization thereat.

28. A method according to claim 16, wherein the second quantity of fluid is a liquid in an amount which is greater than the combined volumes of microbubbles and gaseous $^3He$.

29. A method according to claim 7, wherein the liquid has a low solubility for $^3He$.

30. A method according to claim 15, wherein the fluid is a liquid that has a low solubility for $^3He$.

31. A method according to claim 7, wherein the microbubble material has a high diffusion coefficient for $^3He$.

32. A method according to claim 7, wherein the injectable formulation is sized in the range of above 7 cc's and at or below about 50 cc's.

33. A method according to claim 32, wherein the injectable formulation is sized in the range of between above 7 cc's to about 15 cc's.

34. A method according to claim 7, wherein the quantity of hyperpolarized $^3He$ in the chamber is larger than the quantity of liquid.

35. A method according to claim 7, wherein the quantity of hyperpolarized $^3He$ in the chamber is at least about two times greater than the quantity of liquid.

36. A method according to claim 15, wherein the fluid is a liquid and the bubble solution is an injectable formulation sized in the range of above 7 cc's and at or below about 50 cc's.

37. A method according to claim 36, wherein the injectable formulation is sized in the range of between above 7 cc's to about 15 cc's.

38. A method according to claim 15, wherein the fluid is a liquid and wherein the quantity of hyperpolarized $^3He$ in the chamber is larger than the quantity of liquid.

39. A method according to claim 15, wherein the fluid is a liquid and wherein the quantity of hyperpolarized $^3He$ in the chamber is at least about two times greater than the quantity of liquid.

40. A method according to claim 1, wherein the second quantity of fluid is a liquid that is held in a syringe prior to introducing the second quantity into the container.

41. A method according to claim 40, wherein the syringe is pre-filled with the liquid.

* * * * *

UNITED STATES PATENT AND TRADEMARK OFFICE
CERTIFICATE OF CORRECTION

PATENT NO. : 6,599,497 B2
DATED : July 29, 2003
INVENTOR(S) : Bastiaan Driehuys

It is certified that error appears in the above-identified patent and that said Letters Patent is hereby corrected as shown below:

<u>Column 18,</u>
Line 59, please delete "claim 13" and insert -- claim 15 --

Signed and Sealed this

Twentieth Day of January, 2004

JON W. DUDAS
*Acting Director of the United States Patent and Trademark Office*